(12) United States Patent
Passman et al.

(10) Patent No.: US 10,799,350 B2
(45) Date of Patent: Oct. 13, 2020

(54) PERCUTANEOUS IMPLANT RETRIEVAL CONNECTOR AND METHOD

(71) Applicant: Edwards Lifesciences Corporation, Irvine, CA (US)

(72) Inventors: Joseph Arthur Passman, Costa Mesa, CA (US); Omar Fawzi Azanki, Rancho Santa Margarita, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 189 days.

(21) Appl. No.: 16/222,914

(22) Filed: Dec. 17, 2018

(65) Prior Publication Data

US 2019/0209306 A1    Jul. 11, 2019

Related U.S. Application Data

(60) Provisional application No. 62/614,168, filed on Jan. 5, 2018.

(51) Int. Cl.
*A61F 2/24* (2006.01)
*A61F 2/95* (2013.01)
(Continued)

(52) U.S. Cl.
CPC ...... *A61F 2/2427* (2013.01); *A61B 17/22031* (2013.01); *A61B 17/3468* (2013.01);
(Continued)

(58) Field of Classification Search
CPC ..... A61F 2/2427; A61F 2/95; A61M 39/0247; A61B 17/22031; A61B 17/3468
See application file for complete search history.

(56) References Cited

U.S. PATENT DOCUMENTS

| 3,711,130 A | 1/1973 | Betzler |
| 4,400,022 A | 8/1983 | Wright |

(Continued)

FOREIGN PATENT DOCUMENTS

| WO | 2006127509 A2 | 11/2006 |
| WO | 2007050256 A2 | 5/2007 |

OTHER PUBLICATIONS

Wu et al., "Deformation mechanism of innovatice 3D chiral metamaterials," Scientific Reports; 8:12575, 2018.

(Continued)

*Primary Examiner* — Richard G Louis
(74) *Attorney, Agent, or Firm* — Guy Cumberbatch

(57) ABSTRACT

Devices and methods for retrieving percutaneously implanted catheter systems such as a heart valve repair system. The devices include at least one locking connector at the distal end of a flexible elongated extension for coupling to an implanted tubular member. The locking connector may be a tubular anchor having a pair of distal prongs which are biased outward and face in a proximal direction, as well as an expandable auxetic midsection. Inserting the tubular anchor into the implanted tubular member flexes the distal prongs inward such that they prevent proximal movement of the tubular anchor. A user pulls on the proximal end of the tubular anchor to expand the auxetic midsection and lock the two pieces together. The devices and methods are particularly useful to attach extensions to implanted concentric tubes to enable relative axial force application.

20 Claims, 11 Drawing Sheets

(51) Int. Cl.
*A61B 17/22* (2006.01)
*A61B 17/34* (2006.01)
*A61M 39/02* (2006.01)
*A61B 17/00* (2006.01)

(52) U.S. Cl.
CPC .......... *A61F 2/95* (2013.01); *A61M 39/0247* (2013.01); *A61B 2017/0046* (2013.01); *A61B 2017/00477* (2013.01); *A61B 2017/22035* (2013.01); *A61F 2/2463* (2013.01); *A61F 2/2466* (2013.01); *A61F 2002/9528* (2013.01); *A61F 2002/9534* (2013.01); *A61M 2039/0258* (2013.01); *A61M 2039/0282* (2013.01)

(56) References Cited

U.S. PATENT DOCUMENTS

| | | | |
|---|---|---|---|
| 5,167,239 | A | 12/1992 | Cohen et al. |
| 5,735,842 | A | 4/1998 | Krueger et al. |
| 5,984,568 | A | 11/1999 | Lohbeck |
| 6,050,972 | A | 4/2000 | Zadno-Azizi et al. |
| 6,168,616 | B1* | 1/2001 | Brown, III ................ A61F 2/86 606/108 |
| 6,217,567 | B1 | 4/2001 | Zadno-Azizi et al. |
| 6,241,738 | B1* | 6/2001 | Dereume ......... A61B 17/00234 606/108 |
| 6,273,634 | B1 | 8/2001 | Lohbeck |
| 6,482,228 | B1 | 11/2002 | Norred |
| 6,582,460 | B1* | 6/2003 | Cryer ..................... A61F 2/95 623/1.11 |
| 6,629,534 | B1 | 10/2003 | St. Goar et al. |
| 6,764,510 | B2 | 7/2004 | Vidlund et al. |
| 6,994,092 | B2 | 2/2006 | van der Burg et al. |
| 7,070,616 | B2 | 7/2006 | Majercak et al. |
| 7,077,862 | B2 | 7/2006 | Vidlund et al. |
| 7,160,322 | B2 | 1/2007 | Gabbay |
| 7,320,665 | B2 | 1/2008 | Vijay |
| 7,322,957 | B2 | 1/2008 | Kletschka et al. |
| 7,404,824 | B1 | 7/2008 | Webler et al. |
| 7,678,145 | B2 | 3/2010 | Vidlund et al. |
| 7,785,366 | B2 | 8/2010 | Maurer et al. |
| 7,815,580 | B2 | 10/2010 | Viswanathan |
| 7,854,762 | B2 | 12/2010 | Speziali et al. |
| 7,901,454 | B2 | 3/2011 | Kapadia et al. |
| 7,927,370 | B2 | 4/2011 | Webler et al. |
| 7,942,928 | B2 | 5/2011 | Webler et al. |
| 8,007,428 | B2 | 8/2011 | Vijay |
| 8,070,805 | B2 | 12/2011 | Vidlund et al. |
| 8,092,525 | B2 | 1/2012 | Eliasen et al. |
| 8,133,213 | B2 | 3/2012 | Lashinski |
| 8,216,302 | B2 | 7/2012 | Wilson et al. |
| 8,449,606 | B2 | 5/2013 | Eliasen et al. |
| 8,460,370 | B2 | 6/2013 | Zakay et al. |
| 8,486,136 | B2 | 7/2013 | Maurer et al. |
| 8,579,967 | B2 | 11/2013 | Webler et al. |
| 8,758,430 | B2 | 6/2014 | Ferrari et al. |
| 8,758,432 | B2 | 6/2014 | Solem |
| 8,778,017 | B2 | 7/2014 | Eliasen et al. |
| 8,845,717 | B2 | 9/2014 | Khairkhahan et al. |
| 8,888,843 | B2 | 11/2014 | Khairkhahan et al. |
| 8,888,844 | B2 | 11/2014 | Eliasen et al. |
| 8,932,348 | B2 | 1/2015 | Solem et al. |
| 9,161,837 | B2 | 10/2015 | Kapadia |
| 9,232,998 | B2 | 1/2016 | Wilson et al. |
| 9,232,999 | B2 | 1/2016 | Maurer et al. |
| 9,259,317 | B2 | 2/2016 | Wilson et al. |
| 9,289,297 | B2 | 3/2016 | Wilson et al. |
| 9,474,605 | B2 | 10/2016 | Rowe et al. |
| 9,636,223 | B2 | 5/2017 | Khalil et al. |
| 2003/0050694 | A1 | 3/2003 | Yang et al. |
| 2003/0120341 | A1 | 6/2003 | Shennib et al. |
| 2003/0187494 | A1 | 10/2003 | Loaldi |
| 2004/0098081 | A1 | 5/2004 | Landreville et al. |
| 2004/0225233 | A1 | 11/2004 | Frankowski et al. |
| 2004/0267280 | A1 | 12/2004 | Nishide et al. |
| 2006/0241745 | A1 | 10/2006 | Solem |
| 2007/0027520 | A1* | 2/2007 | Sherburne ............ A61M 25/10 623/1.11 |
| 2007/0162071 | A1 | 7/2007 | Burkett et al. |
| 2007/0198082 | A1 | 8/2007 | Kapadia et al. |
| 2007/0219627 | A1 | 9/2007 | Chu et al. |
| 2007/0255399 | A1 | 11/2007 | Eliasen et al. |
| 2007/0265700 | A1 | 11/2007 | Eliasen et al. |
| 2007/0270943 | A1 | 11/2007 | Solem et al. |
| 2007/0282429 | A1 | 12/2007 | Hauser et al. |
| 2009/0048668 | A1 | 2/2009 | Wilson et al. |
| 2009/0069885 | A1 | 3/2009 | Randert et al. |
| 2009/0137968 | A1 | 5/2009 | Rottenberg |
| 2010/0022948 | A1 | 1/2010 | Wilson et al. |
| 2010/0198347 | A1 | 8/2010 | Zakay et al. |
| 2010/0298929 | A1 | 11/2010 | Thornton et al. |
| 2011/0077733 | A1 | 3/2011 | Solem |
| 2011/0184512 | A1 | 7/2011 | Webler et al. |
| 2011/0224784 | A1 | 9/2011 | Quinn |
| 2012/0143320 | A1 | 6/2012 | Eliasen et al. |
| 2013/0338763 | A1 | 12/2013 | Rowe et al. |
| 2014/0309732 | A1 | 10/2014 | Solem |

OTHER PUBLICATIONS

Wu et al., "Mechanical Properties of Anti-Tetrachiral Auxetic Stents," Composite Structures, vol. 185, Feb. 1, 2018.

* cited by examiner

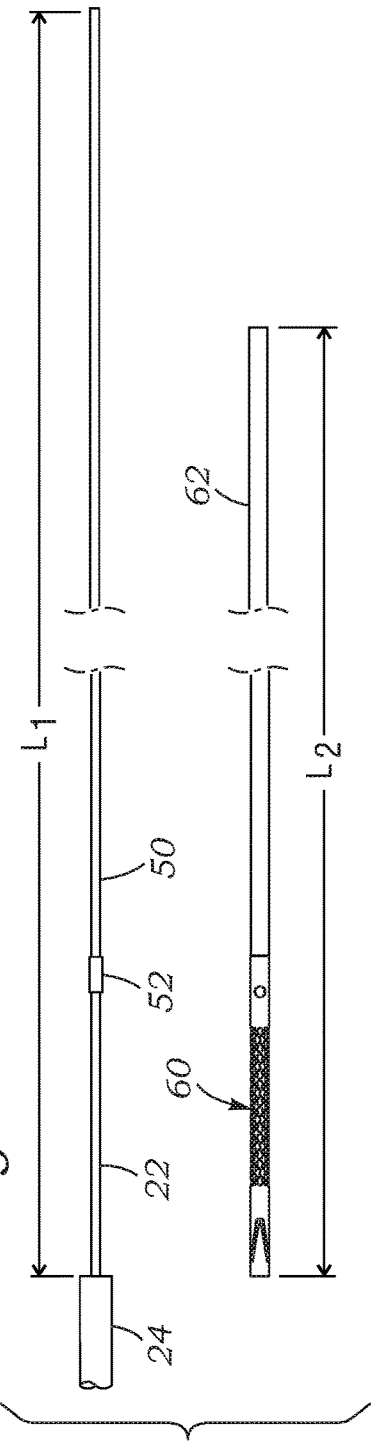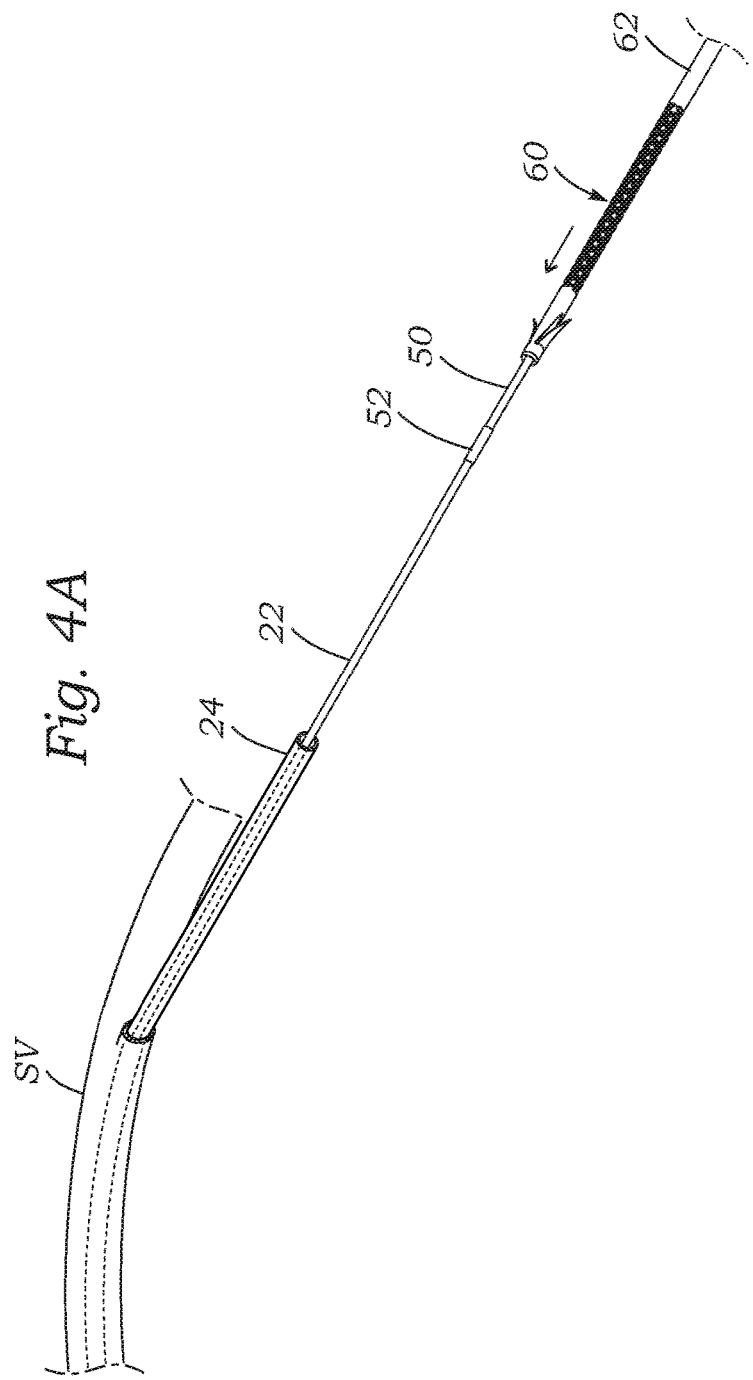

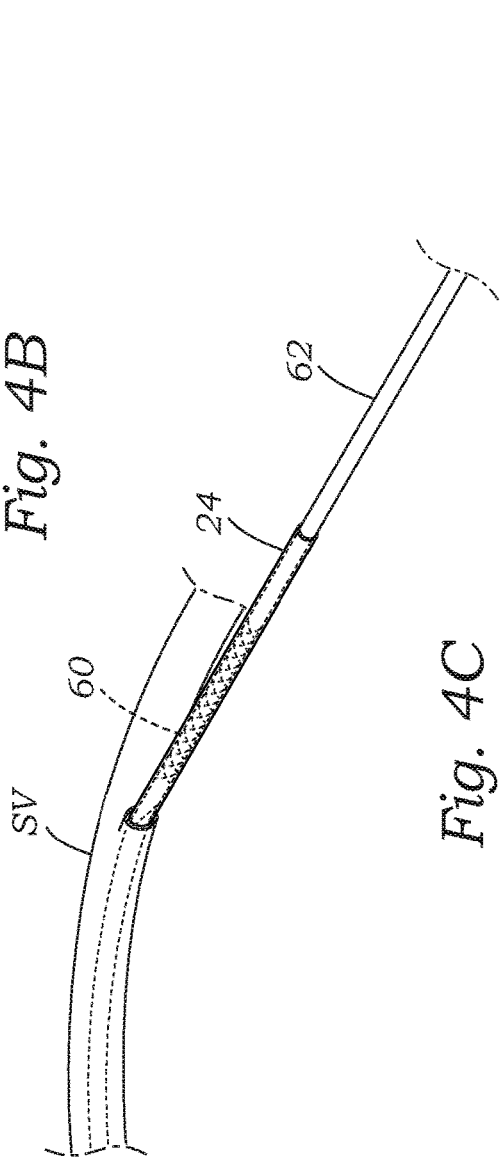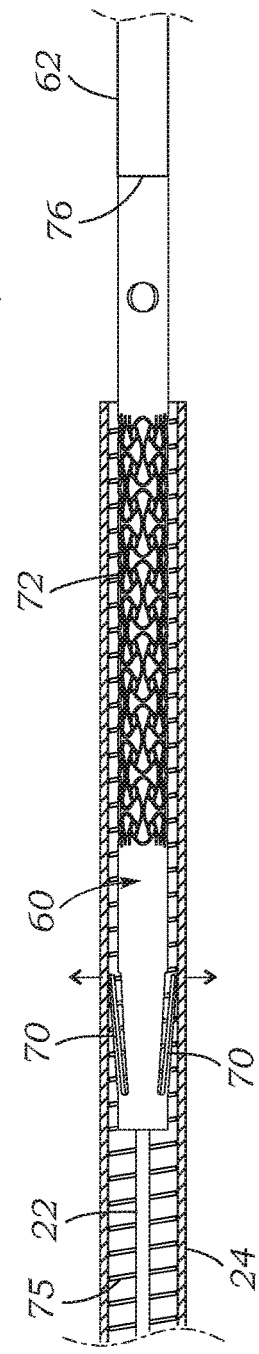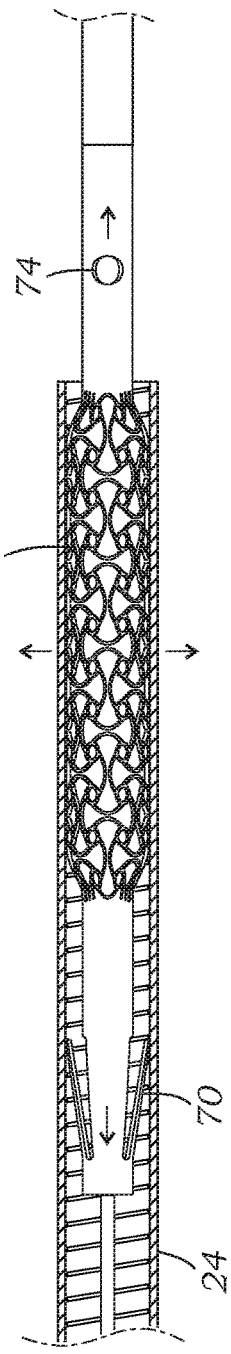

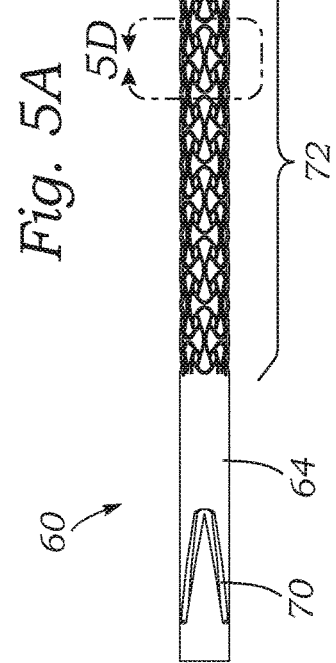
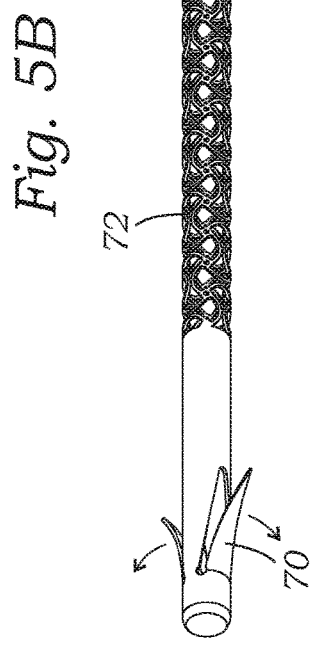
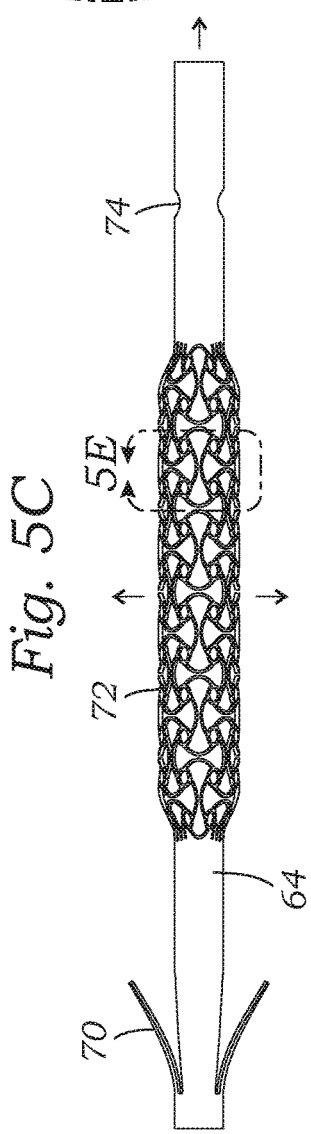
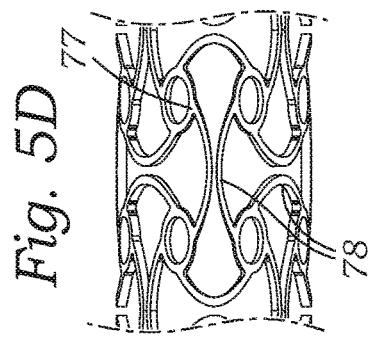
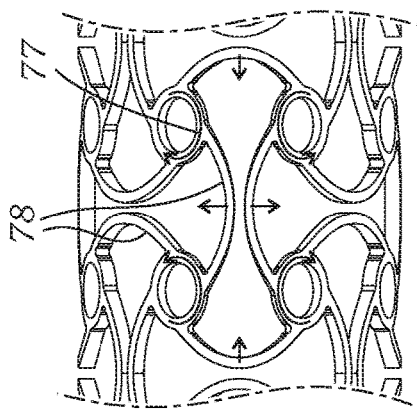

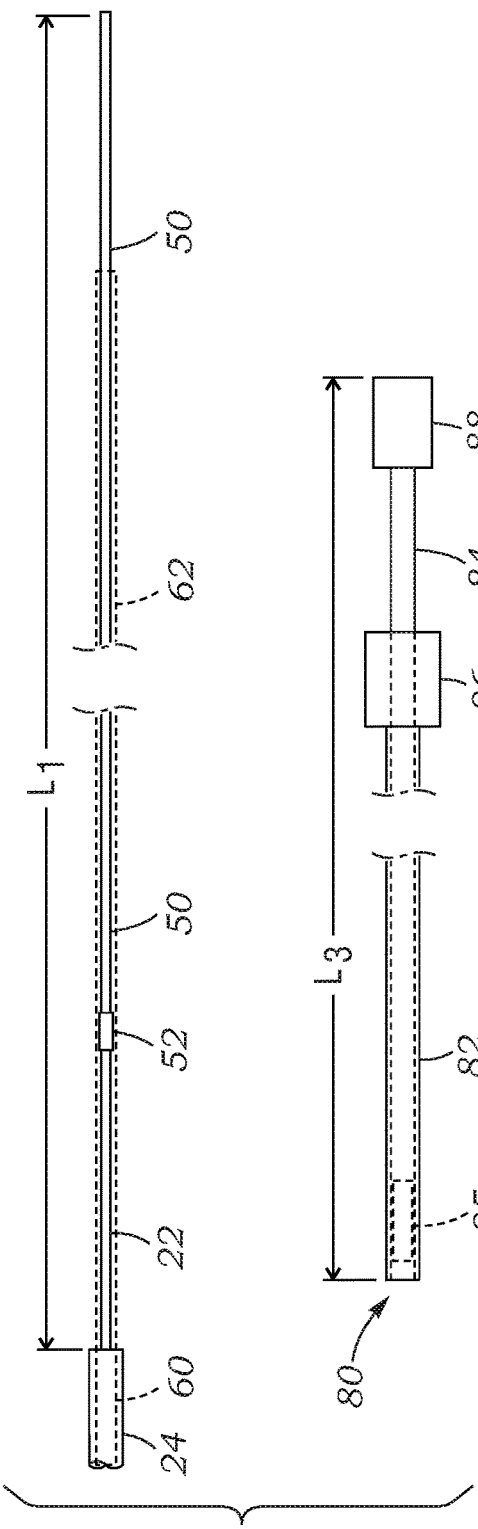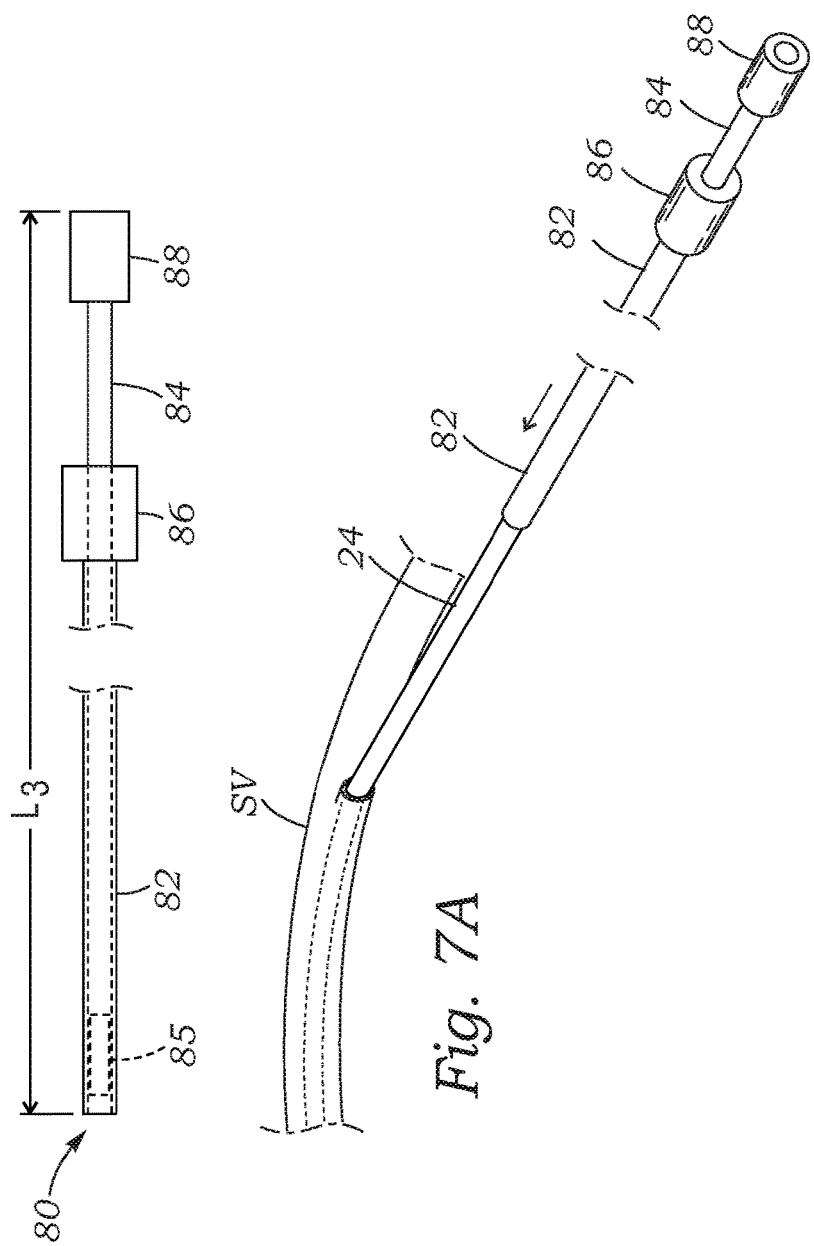

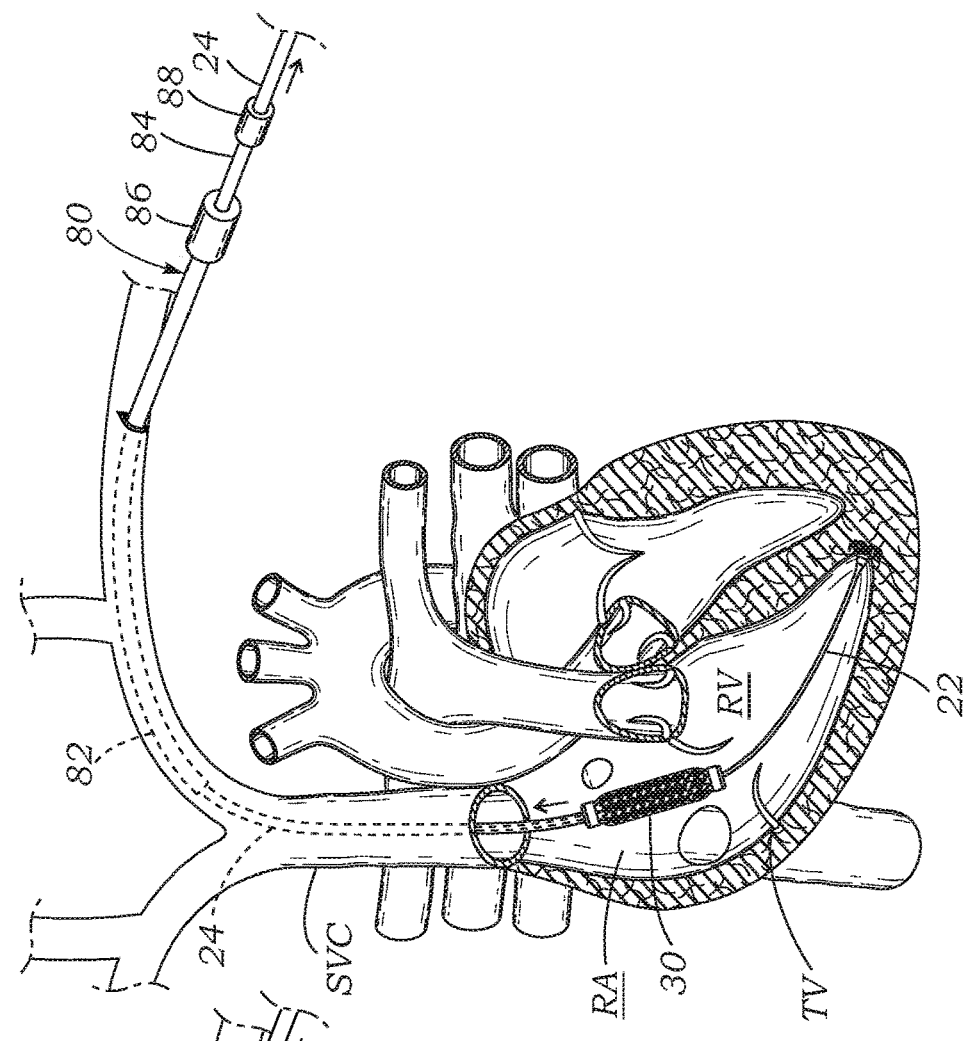
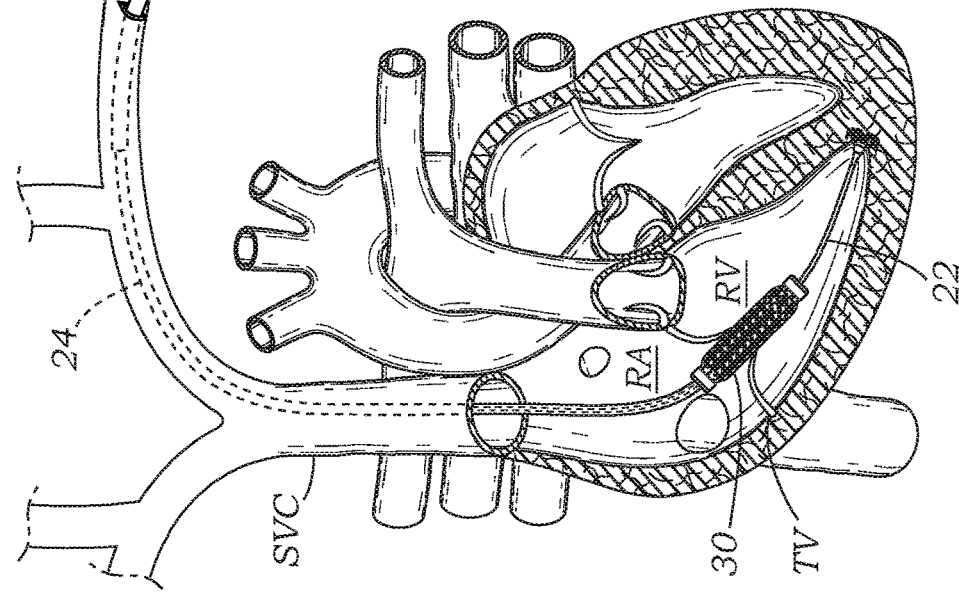

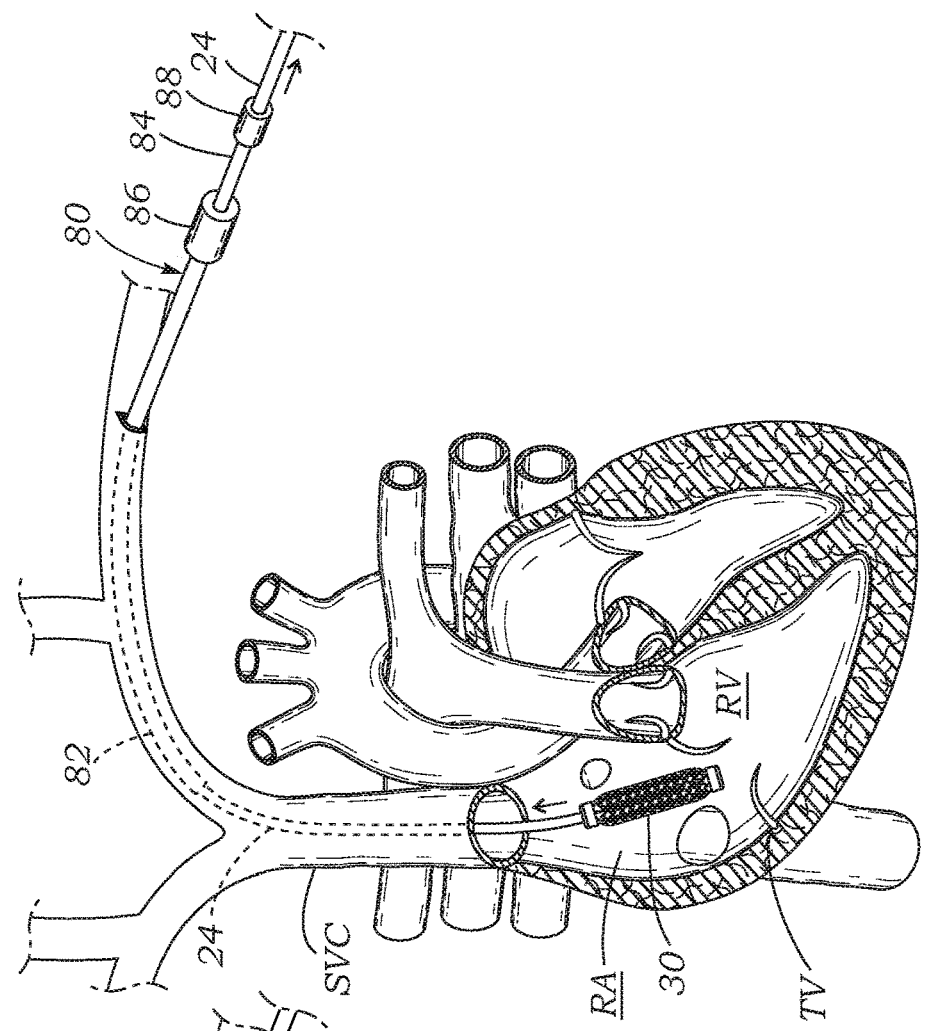
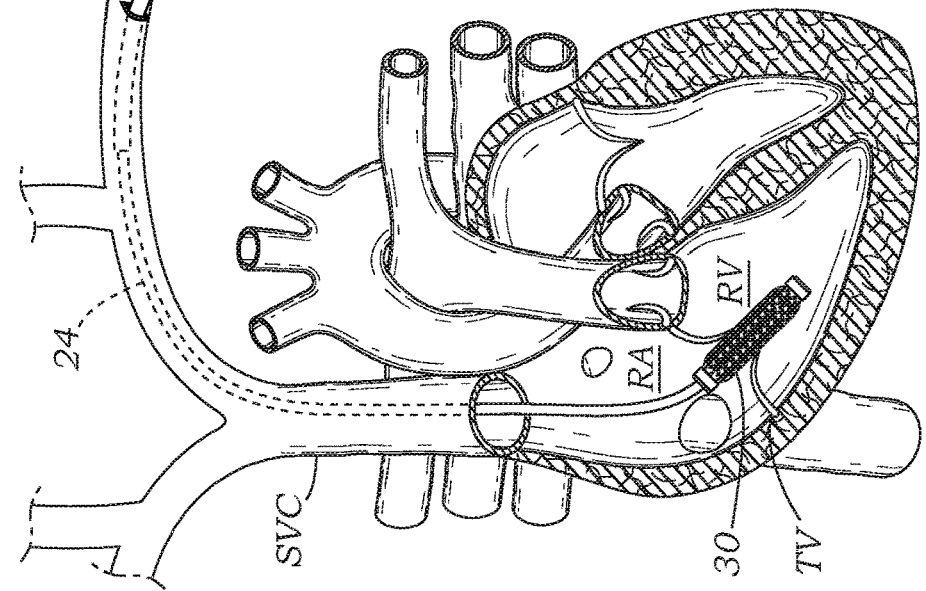

PERCUTANEOUS IMPLANT RETRIEVAL CONNECTOR AND METHOD

RELATED APPLICATIONS

The present application claims priority to U.S. Provisional Application No. 62/614,168, filed Jan. 5, 2018, the contents of which are expressly incorporated herein.

TECHNICAL FIELD

The present disclosure relates generally to devices and methods for retrieving minimally-invasive or percutaneously-delivered catheter systems such as a heart valve repair system.

BACKGROUND

Heart valve disease, such as valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous.

One solution is seen in U.S. Pat. No. 9,474,605 which discloses a heart valve repair system for reducing regurgitation through a native valve. A flexible rail having a ventricular anchor on the distal end thereof adapted to anchor into tissue within a ventricle is first deployed percutaneously. A repair catheter passes along the flexible rail, and a leaflet coaptation member on a distal end of the catheter is located within the native valve leaflets. Once placed correctly, the coaptation member reduces or eliminates regurgitation through the native valve, in particular a tricuspid heart valve. Real time visualization ensures proper leaflet coaptation and regurgitation reduction, and then a locking collet on the repair catheter secures the axial position of the coaptation member and repair catheter on the flexible rail. If the device does not function properly or in case of any other difficulties, it is relatively simple at this stage to retrieve the catheter and flexible rail with anchor. If all is well, the proximal end of the repair catheter is then severed beyond the locking collet, and the terminal end secured subcutaneously, typically adjacent the subclavian vein. Should there be any subsequent anomalies in response to the device implantation, such as a reduction in diameter of the tricuspid annulus, infection, thrombus, late anchor dislodgement, or endocarditis, retrieval of the device is difficult.

Consequently, there is a need for a way to retrieve the heart valve repair system and percutaneously delivered devices like it after implant.

SUMMARY

The present disclosure relates generally to devices and methods for retrieving minimally-invasive or percutaneously-delivered catheter systems, such as a heart valve repair system, having concentrically-disposed inner and outer tubes. Such a retrieval system should have the ability to move the inner and outer tubes independently.

A system for retrieving an elongated percutaneously-implanted implant or instrument having a tubular shaft that defines a lumen is disclosed. The system includes a flexible extension member having a connector that extends within the lumen of the tubular shaft and attaches thereto, the flexible extension member having a length. The connector comprises an expandable auxetic section that radially expands into contact with the lumen when subjected to a tensile force. In one embodiment, the percutaneously-implanted implant or instrument has concentrically-disposed inner and outer tubes, and the retrieval system has two extension members; one for the inner shaft and one for the outer shaft. In use, a flexible extension member is attached to the inner tube with a first connector, the flexible extension member having a first length, and a tubular extension member is then attached to the outer tube with a second connector, the tubular extension member having a second length shorter than the first length. The tubular extension member has an inner lumen sufficiently large to slide over the flexible extension member, first connector, and inner tube, and an outer diameter small enough to fit within the outer tube lumen. At least one of the first and second connectors comprises an expandable auxetic section that radially expands into contact with the respective inner or outer tube lumen when subjected to a tensile force.

A method for retrieving an elongated percutaneously-implanted implant or instrument having a tubular shaft that defines a lumen is disclosed. The method includes accessing a proximal end of the tubular shaft. A flexible extension member is attached to the tubular shaft with a connector that extends within the lumen thereof, the flexible extension member having a length. The connector comprises an expandable auxetic section that radially expands into contact with the lumen when subjected to a tensile force. A method for retrieving an elongated percutaneously-implanted device including concentrically-disposed inner and outer tubes is also disclosed. The method includes accessing proximal ends of both of the inner and outer tubes that each define lumens. A flexible extension member is attached to the inner tube with a first connector, the flexible extension member having a first length. A tubular extension member is then attached to the outer tube with a second connector. The tubular extension member has a second length shorter than the first length. Also, the tubular extension member has an inner lumen sufficiently large to slide over the flexible extension member, first connector, and inner tube, and an outer diameter small enough to fit within the outer tube lumen. At least one of the first and second connectors comprises an expandable auxetic section that radially expands into contact with the respective inner or outer tube lumen when subjected to a tensile force.

The present application provides an implement for connecting the inner diameter of tubing to an extending element, the implement including an anchoring prong and an auxetic, swelling midsection for a doubly-reinforced inner diameter connection that maintains lumen patency. In the proposed connection solution, the distal end of a connection stent is inserted into the inner diameter of a tube to which a connection is desired. Outwardly-bent anchoring prongs flex inward like barbs as the stent is inserted. As the stent is inserted, compressive stress is exerted on the axial direction of the stent. The OD of the stent decreases due to the unique properties of a laser-cut anti-tetrachiral pattern in the midsection, easing insertion. Once the stent is completely inserted, the connection is made. The user can then pull proximally on the stent which engages the barb with the ID of the tubing and creates an anchoring point. As the user exerts additional stress in the proximal direction, the laser-cut stent pattern expands outward, creating additional anchoring fixation to strengthen the tubing connection all while relieving some of the stress on the tubing at the location of the anchoring prong.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 3 illustrates a full length of the rail extension member attached to the anchor rail and a full-length of a shaft extension member that couples to a catheter shaft, both in broken line;

FIG. 4A illustrates an initial step in coupling the outer shaft extension member to the catheter shaft by passing a shaft anchor and its extension over the rail extension member, while FIG. 4B shows the shaft extension member coupled to the catheter shaft;

FIGS. 4C-4D are enlarged sectional views illustrating constructional details of the shaft anchor after insertion and expansion within the catheter shaft to couple the two elements together;

FIGS. 5A-5E are elevational, perspective and enlarged views of the shaft anchor showing operation of an auxetic expandable section;

FIG. 6 illustrates the rail extension member attached to the repair catheter, the shaft extension member that couples to the catheter shaft thereover, and a full-length of a removal catheter that slides over the shaft extension member, each in broken line;

FIG. 7A illustrates an initial step in advancing the removal catheter over the shaft extension member, while FIGS. 7B and 7C show the removal catheter advanced into the subclavian vein and initial retraction of the catheter shaft and the coapting element thereon from within the tricuspid valve;

FIGS. 7D and 7E show the system of FIG. 1A and a removal catheter advanced into the subclavian vein and initial retraction of the catheter shaft and the coapting element thereon from within the tricuspid valve;

DETAILED DESCRIPTION OF THE PREFERRED EMBODIMENTS

The following description refers to the accompanying drawings, which illustrate specific embodiments. Other embodiments having different structures and operation do not depart from the scope of the present disclosure.

Various embodiments of the present disclosure are directed to devices and methods for removing implanted elongated devices from the body. The most common implanted elongated devices include minimally-invasive or percutaneously-delivered catheter systems, though other devices are contemplated. More specifically, the application pertains to devices and methods for coupling extenders to an implanted elongated device to permit advancement of retrieval or removal implements along the implanted device deep into the body.

A particular application of such devices and methods disclosed herein involves removal of an implanted heart valve regurgitation reduction system, which may be implanted within the left or right side of the heart and extends out of the heart into the vasculature, for example, to the subclavian vein. However, the principles disclosed herein that permit removal of such an implanted device are suitable for other applications as well. For example, the presently disclosed devices and methods may be adapted for removing such items as pacemakers or monitors implanted in the heart. Other implanted devices that include an elongated element accessible from close to the surface of the body (e.g., subcutaneously) may also be retrieved using the devices and methods disclosed herein.

Figure 1:
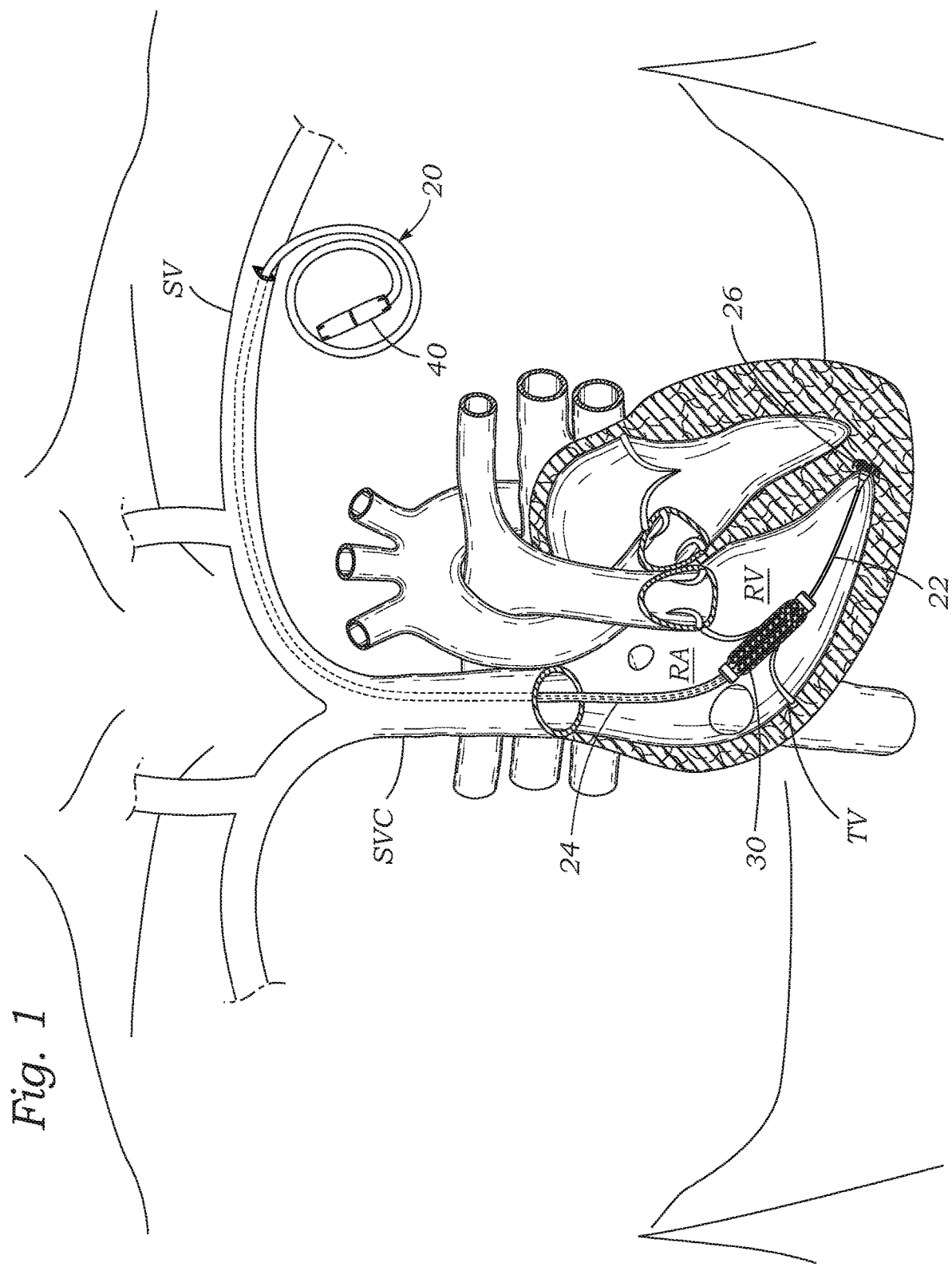
FIG. 1 is a schematic view of the final configuration of a percutaneous heart valve regurgitation reduction system having a coapting element positioned within the tricuspid valve and a proximal length of the repair catheter including a locking collet shown exiting the subclavian vein to remain implanted subcutaneously.

FIG. 1 is a schematic view of the implanted configuration of a percutaneous heart valve regurgitation reduction system having a coapting element positioned within the tricuspid valve and a proximal length of the repair catheter including a locking collet shown exiting the subclavian vein to remain implanted subcutaneously. The system includes a repair catheter 20 percutaneously delivered into the right side of the heart to reduce tricuspid valve TV regurgitation. The repair catheter 20 enters the right atrium RA from the superior vena cava SVC after having been introduced to the subclavian vein SV using well-known methods, such as the Seldinger technique. The repair catheter 20 preferably tracks over a smaller diameter pre-installed anchor rail 22 that has also been inserted into the subclavian vein SV and steered through the vasculature until it resides and is anchored at or near the apex of the right ventricle RV, as shown. The repair catheter 20 includes an elongated hollow shaft 24 that may be reinforced, for example, with an embedded braided or coiled structure.

A distal device anchor 26 secures a distal end of the rail 22 at the apex of the right ventricle RV, or to other anatomical features within the ventricle. The anchor rail 22 may be constructed as a braided wire rod, or cable, and is desirably hollow so as to enable passage over a guide wire (not shown). Further details of the anchor rail 22 and device anchor 26 are seen in U.S. Pat. Nos. 8,932,348 and 9,474, 605, the entire disclosures of which are expressly incorporated herein by reference.

The repair catheter shaft 24 carries a spacer or coapting element 30 on its distal end portion that is ultimately positioned within the tricuspid valve TV, the leaflets of which are shown closed in systole and in contact with the coapting element 30. A variety of coapting elements may be utilized, the common feature of which is the goal of providing a plug of sorts within the heart valve leaflets to mitigate or otherwise eliminate regurgitation. In the illustrated embodiment, the coapting element 30 includes an expandable body that may be adjusted in vivo. Other coapting elements are disclosed in U.S. Pat. Nos. 9,474,605 and 9,636,223, the entire disclosures which are expressly incorporated herein by reference. The coapting element 30 is delivered in a radially contracted state to reduce the size of the incision used and facilitate passage through the vasculature, and is then expanded within the valve leaflets.

In one preferred embodiment, the coapting element 30 includes an auxetic structure that expands when subjected to longitudinal tensile force. More particularly, the coapting element 30 includes a midsection having negative Poisson's ratio properties. Examples of such structures include a laser-cut, pre-compressed anti-tetrachiral pattern such as described below with respect to a connector for the retrieval system.

A locking mechanism is provided on the regurgitation repair catheter 20 to lock the axial position of the coapting element 30 within the tricuspid valve TV and relative to the fixed anchor rail 22. For example, a locking collet 40 along the length of the repair catheter shaft 24 permits the physician to selectively lock the position of the shaft, and thus the connected coapting element 30, along the anchor rail 22. There are of course a number of ways to lock a catheter over a concentric guide rail, and the application should not be considered limited to the illustrated embodiment. For instance, rather than a locking collet 40, a crimpable section such as a stainless steel tube may be included on the repair catheter shaft 24 at a location near the skin entry point and spaced apart from the location of the coapting element 30. The physician need only position the coapting element 30 within the leaflets, crimp the catheter shaft 24 onto the anchor rail 22, and then sever both the catheter and rail above or proximal to the crimp point.

A proximal length of the repair catheter 20 including the locking collet 40 exits the subclavian vein SV through a sealed puncture and remains implanted subcutaneously; preferably coiling upon itself as shown. In the procedure, the physician first ensures proper positioning of the coapting element 30 within the tricuspid valve TV, locks the repair catheter 20 with respect to the anchor rail 22 by actuating the locking collet 40, and then severs that portion of the repair catheter shaft 24 that extends proximally from the locking collet. The collet 40 and/or coiled portion of the repair catheter shaft 24 may be sutured or otherwise anchored in place to subcutaneous tissues outside the subclavian vein SV. It is also worth noting that because the repair catheter 20 initially slides with respect to the anchor rail 22, it may be completely removed to withdraw the coapting element 30 and abort the procedure during implantation. The implant configuration is similar to that practiced when securing a pacemaker with an electrode in the right atrium muscle tissue and the leads extending to the associated pulse generator placed outside the subclavian vein. Indeed, the procedure may be performed in conjunction with the implant of a pacing lead.

Prior to locking the catheter shaft 24 onto the anchor rail 22 and severing both, relative linear movement of the two tubes is enabled from their proximal ends. More particularly, these concentric tubes extend a sufficient distance out of the body to be manipulated manually. The length of the inner tube (anchor rail 22) is greater than the length of the outer tube (catheter shaft 24) so that relative sliding movement is easily accomplished by grabbing or grasping, and displacing the proximal ends with respect to one another, thus providing a sufficient degree of control to implant and conversely retrieve the devices. For instance, the same instrument that delivers the anchor rail 22 and its device anchor 26 may be deployed through the catheter shaft 24 to collapse the anchor, such as to reposition or even retrieve it.

However, once the repair catheter 20 is locked onto the anchor rail 22 and severed, it is difficult to manipulate and problematic to achieve or effect removal of either device. That is, relatively short lengths of these components remain to access outside the vasculature, and it becomes difficult to grab and displace them relative to each other. The anchor rail 22 is embedded into the ventricular tissue with the device anchor 26, and the coapting element 30 is too large in its implanted configuration to be removed through the vasculature—it must first be reduced in size. Unfortunately, inserting elongated removal devices down the system, either within or on the outside of the repair catheter 20, is hindered by the short length of the repair catheter shaft 24 available to grab onto. The present application provides devices and methods for attaching extenders to the concentrically arranged catheter shaft 24 and anchor rail 22 so as to permit subsequent advancement of removal devices thereover. In addition to providing added length to the concentric tubes, the extenders are securely coupled to the tubes and permit the application of relative longitudinal force thereto. That is, the connectors and extenders enable independent movement and thus control of the rail 22 and catheter shaft 24.

Figure 1A:
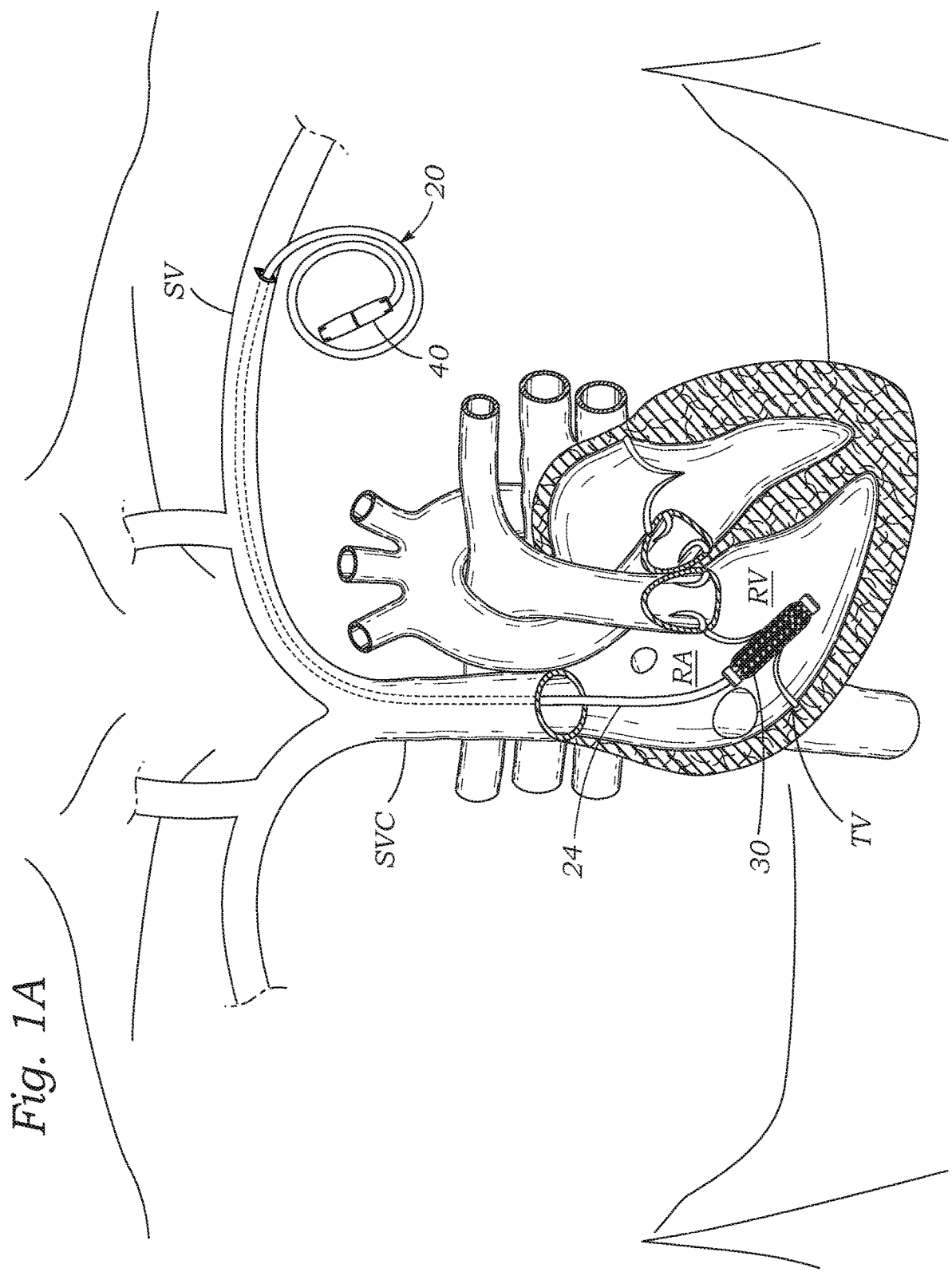
FIG. 1A is a schematic view of a percutaneous heart valve regurgitation reduction system similar to that of FIG. 1 but without an anchor rail.

FIG. 1A shows a percutaneous heart valve regurgitation reduction system similar to that of FIG. 1 but without the aforementioned anchor rail 22 and its distal device anchor 26. In this system, the coapting element 30 is left unanchored within the tricuspid valve, or secondary anchors (not shown) may be utilized. Since the system only has one main tube, a retrieval system need not have the capacity for grasping concentric tubes, as will be explained below with reference to FIGS. 7D and 7E.

Figure 2A:
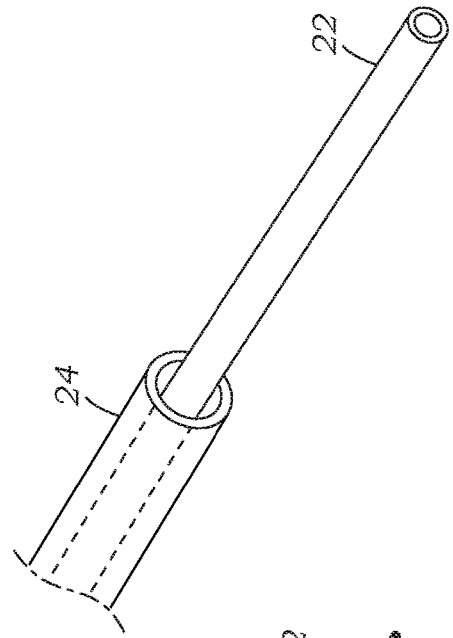
FIG. 2A is an isolated view of a proximal length of the repair catheter indicating a preferred severance of a proximal end thereof.
Figure 2B:
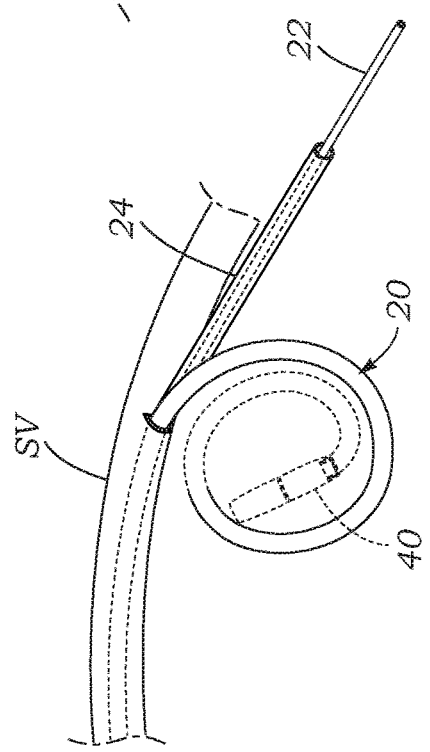
FIG. 2B is an enlarged view of the proximal end of the repair catheter.

FIG. 2A is an isolated view of a proximal length of the repair catheter 20 indicating a preferred severance of a proximal end thereof, and FIG. 2B is an enlarged view of the proximal end of the repair catheter. The first step in retracting the coapting element 30 and its shaft 24 involves forming an access opening to the subcutaneous tissue outside of the subclavian vein. The repair catheter shaft 24 and anchor rail 22 are then severed distal to the locking structure. Preferably, the catheter shaft 24 is severed farther down its length than the anchor rail 22, such that the anchor rail extends proximally beyond the shaft as shown. For example, the anchor rail 22 may extend between about 3-10 cm from within and out of the catheter shaft 24.

Severing the concentric tubes of the catheter shaft 24 and anchor rail 22 in this manner may be done with various tools. For instance, the Accu-Cut Oval Head Hard Wire Cutter from Penn Tool Co. of Maplewood, N.J. may be used to cut catheters. Alternatively, various medical tube cutters are available from The Eraser Company of Syracuse, N.Y., and from Lakeview Equipment of Chicago, Ill. Finally, there are a number of manually-operated tube cutters on the market which may be used to sever only an outer tube such as the catheter shaft 24 concentrically-disposed around an inner tube such as the anchor rail 22; for example various tools from Universal Grinding Corporation of Cleveland, Ohio or the Excelta medical tube cutter from Jensen Tools and Supply of North Andover, Mass.

Figure 2C:
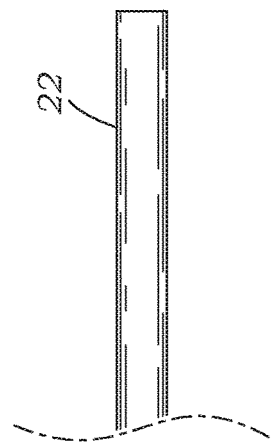
FIGS. 2C and 2D show exploded and assembled views of the coupling of an inner rail extension member to a hollow anchor rail that forms part of the repair catheter.
Figure 2D:
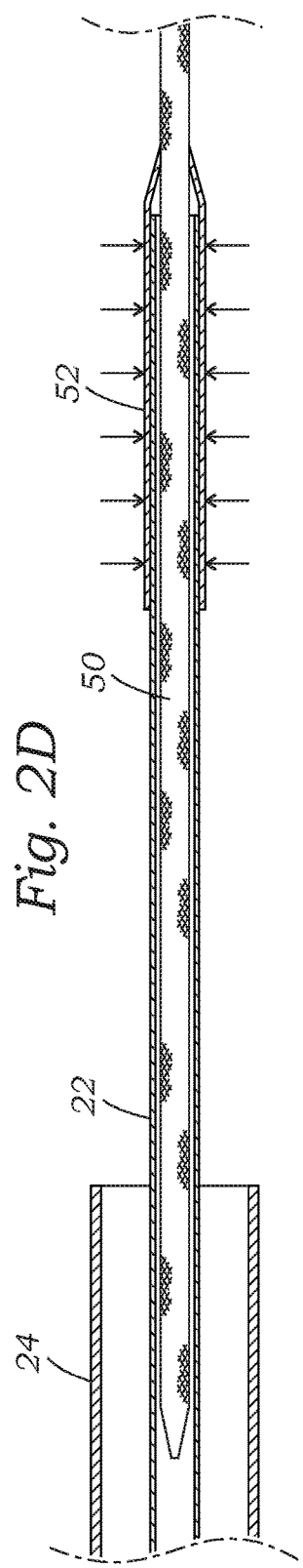

FIGS. 2C and 2D show exploded and assembled views of a second step in the procedure involving the coupling of a first or inner rail extension member 50 to the hollow anchor rail 22. The rail extension member 50 preferably comprises an extension cable which terminates in a tapered tip 51. The tapered tip 51 and extension cable are small enough to fit within the lumen of the anchor rail 22, and the user guides the rail extension member 50 a short distance into the hollow anchor rail 22. A hypo tube 52, which is laser-welded onto the extension cable 50, is then crimped over the anchor rail 22. This provides the user with an extended length for the anchor rail 22 of approximately the same diameter so that it can be displaced or held relative to the repair catheter shaft 24, as will be seen. Other solutions for coupling the rail extension member 50 to the anchor rail 22 are contemplated and a crimpable hypo tube 52 should not be considered limiting. For instance, an auxetic anchor, as will be described below, may be utilized.

FIG. 3 illustrates a full length of the rail extension member 50 attached to the anchor rail 22 and a full-length of a shaft anchor 60 and a second or shaft extension member 62 that eventually couples to the catheter shaft 24, as will be shown. As mentioned, the rail extension member 50 couples to the anchor rail 22 via the crimped hypo tube 52. The resulting length $L_1$ of the combined anchor rail 22 protruding from the shaft 24 and its extension 50 is shown, and is desirably sufficient to enable subsequent advancement of elongated retrieval devices thereof. For example, the length $L_1$ may be about 450-600 millimeters. In contrast, a length $L_2$ of the shaft anchor 60 and shaft extension member 62 is less than the length $L_1$. For instance, the length $L_2$ may be about 300-400 millimeters.

In a preferred embodiment, the shaft anchor 60 is a relatively rigid tubular structure that couples to a relatively flexible tubular shaft extension member 62. Coextensive inner lumens of the shaft anchor 60 and shaft extension member 62 are sized slightly larger than the anchor rail 22 and its extension 50, and preferably slightly larger than the crimped hypo tube 52 therebetween. This permits the combined anchor 60 and shaft extension member 62 to slide over the assembly of the anchor rail 22 and its extension 50, as will be explained. Further details of the shaft anchor 60 will be provided below.

FIG. 4A illustrates an initial step in coupling the outer shaft anchor 60 and shaft extension member 62 to the catheter shaft 24 by passing the shaft extension member over the rail extension member 50. As mentioned, the common lumens of the anchor 60 and extension 62 are sized to pass easily over the anchor rail 22 and its extension 50. At the same time, a coextensive outer diameter of the assembly of the shaft anchor 60 and extension 62 is sized to pass within the lumen of the catheter shaft 24. FIG. 4B shows the shaft anchor 60 extended within the catheter shaft 24 and coupled thereto, with the shaft extension member 62 extending proximally therefrom.

FIGS. 4C-4D are enlarged sectional views illustrating constructional details of the shaft anchor 60 and extension 62 after insertion and expansion within the catheter shaft 24 to couple the two elements together. Reference is also made to FIGS. 5A-5E showing operation of an auxetic expandable section of the shaft anchor 60. The shaft anchor 60 general comprises a rigid tubular body 64 having a plurality of V-shaped barbs 70 cut into a distal end thereof. There are preferably two barbs 70 on diametrically opposite sides of the tubular body 64 which are cantilevered and taper down in a proximal direction; i.e., they point proximally. The barbs 70 are formed such as by heat treating to have an outward bias, as indicated in FIGS. 5B and 5C. The shaft anchor 60 further includes a central expandable section 72 and may also include a pair of diametrically-opposed eyeholes 74 in a proximal end of the tubular body 64. The expandable section 72 comprises an auxetic structure that is configured to radially expand upon being subjected to longitudinal or axial tensile force. A short explanation of auxetic structures is appropriate.

Poisson's ratio expresses the relative nature of a material to contract or expand transversely under axial strain. Most materials contract transversely when subjected to axial strain. This behavior results in a positive Poisson's ratio. The opposite behavior—expanding under axial loading—results in a negative Poisson's ratio. An auxetic (or negative Poisson's ratio) material expands in all directions when pulled in only one, behaving in an opposite way as compared with "classical" materials. Chiral shape-memory-alloy honeycombs have been discussed in the scientific literature for their abilities to exhibit negative Poisson's ratio. The expandable section 72 of the shaft anchor 60 has a laser-cut, pre-compressed anti-tetrachiral pattern.

With reference to FIGS. 4C-4D, as the shaft anchor 60 passes into the repair catheter shaft 24, the distal barbs 70 are flexed inward by the smaller lumen size of the shaft. At the same time, compression placed on the shaft 60 helps to reduce the radial diameter of the expandable midsection 72 by virtue of its negative Poisson's ratio. Ultimately, the user advances the shaft anchor 60 at least as far as the expandable midsection 72 is fully within the catheter shaft 24, as shown.

The barbs 70 point in a proximal direction, and are biased outward to interact with the luminal wall of the repair catheter shaft 24, and preferably with a helical stiffening coil 76 therein, to help prevent proximal movement of the shaft anchor 60. That is, the distal barbs 70 contact and anchor inside of the repair catheter shaft 24 so as to provide an anchor against proximal movement of the shaft 24 so as to create tension in the expandable auxetic section 72. As explained, the expandable midsection 72 of the shaft anchor 60 is formed of an auxetic structure which expands when placed into tension. By pulling on the proximal end of the shaft anchor 60 while holding the repair catheter shaft 24 beyond the shaft anchor, the midsection 72 can be expanded to anchor the shaft anchor 60 within the repair catheter shaft 24. The eyeholes 74 in the proximal end of the shaft anchor 60 may be utilized to pass a small linear implement to form a "T" through the tubular body 64 to help in applying tension to the shaft anchor. Alternatively, a coupling junction 76 between the shaft anchor 60 and the shaft extension member 62 may be robust enough to enable tension to be applied by simply pulling on the shaft extension.

FIGS. 5D and 5E illustrate an exemplary laser-cut anti-tetrachiral pattern before and after expansion, respectively. The pattern includes a plurality of evenly-spaced circular rings or hubs 77 connected to other adjacent hubs by arcuate struts 78. In the illustrated embodiment, the pattern features sets of four adjacent circular hubs 77 forming a square or rectangle around the tubular midsection 72 each connected by four arcuate struts 78. Pulling on the ends of the expandable midsection 72 tends to straighten the arcuate struts 78 which generally aligned with the longitudinal axis of the device. Movement arrows are shown on two of these longitudinally-oriented struts 78 which tend to move away from one another. At the same time, this movement tends to rotate the connected circular hubs 77, as shown by the rotational movement arrows. Both the spreading a part of the longitudinally-oriented struts 78 and the rotation of the circular hubs 77 tends to straighten out the circumferentially-oriented struts 78, as shown.

Of course, other such patterns may be utilized to result in an auxetic structure having a negative Poisson's ratio. It should be understood, therefore, that other expandable structures with negative Poisson's ratio may be used, such as various anti-tetrachiral patterns. Most materials have Poisson's ratio values ranging between 0.0 and 0.5. A perfectly incompressible material deformed elastically at small strains would have a Poisson's ratio of exactly 0.5. Some materials, e.g. some polymer foams, origami folds, and certain cells can exhibit negative Poisson's ratio, and are referred to as auxetic materials. If these auxetic materials are stretched in one direction, they become thicker in the perpendicular direction. In contrast, some anisotropic materials, such as carbon nanotubes, zigzag-based folded sheet materials, and honeycomb auxetic metamaterials to name a few, can exhibit one or more Poisson's ratios above 0.5 in certain directions. For instance, Wu, et al. describes a number of alternative anti-tetrachiral patterns in "Deformation mechanism of innovative 3D chiral metamaterials," SCIENTIFIC REPORTS; 8:12575 (2018), the disclosure of which is hereby expressly incorporated by reference. Likewise, Wu, et al. disclose anti-tetrachiral stent patterns in "Mechanical properties of anti-tetrachiral auxetic stents," Composite Structures, Volume 185-Feb. 1, 2018), the disclosure of which is hereby expressly incorporated by reference.

FIG. 6 illustrates the rail extension member 50 attached to the repair catheter shaft 24, with the assembly of the shaft anchor 60 and shaft extension member 62 thereover, and a full-length of a removal catheter 80 that slides over the shaft extension, each in broken line. As described above with respect to FIG. 3, the length $L_1$ of anchor rail 22 and its extension is longer than the length $L_2$ of shaft anchor 60 and its extension 62. At the same time, the length $L_2$ (and also length $L_1$) is longer than the length $L_3$ of the removal catheter 80, so that when the removal catheter extends over the anchor rail 22 and catheter shaft 24, the shaft extension member 62 projects proximally therefrom to enable it to be manipulated.

The removal catheter 80 comprises an elongated sheath 82 having an inner luminal diameter sized large enough to pass over the assembly of the shaft anchor 60 and extension 62. An elongated device retrieval catheter 84 passes through a proximal hub 86 of the removal catheter 80 and has a length that enables it to extend through and beyond a distal end of the elongated sheath 82. As will be described below, a distal end of the retrieval catheter 84 includes an expandable retrieval cage 85, while a proximal end has a hub 88 with hemostasis valves therein. The inner luminal diameter of the retrieval catheter 84 including the retrieval cage 85 is also sized large enough to pass over the assembly of the shaft anchor 60 and extension 62.

FIG. 7A illustrates an initial step in advancing the removal catheter 80 over the catheter shaft 24, while FIGS. 7B and 7C show the removal catheter 80 advanced into the subclavian vein and initial retraction of the catheter shaft 24 and the coapting element 30 thereon from within the tricuspid valve. The removable catheter sheath 82 with the retrieval catheter 84 therein is first advanced over the proximal end of the anchor rail extension member 50, and then over the proximal portion of the shaft extension member 62, as seen in FIG. 6. The user advances the catheter sheath 82 until its distal end slides over the catheter shaft 24. The distal tip of the catheter sheath 82 may be slightly tapered to facilitate entry through the puncture wound into the subclavian vein SV.

With reference to FIG. 7B, the removal catheter sheath 82 advances over the catheter shaft 24 and along a predetermined distance of the subclavian vein SV and halts approximately at the beginning of the superior vena cava SVC, as shown in FIG. 7C.

FIG. 7C also illustrates proximal retraction of the repair catheter shaft 24 toward the removal sheath 82 such that the coapting element 30 eventually comes into proximity with the distal end of the removal sheath. During this process, the rail extension member 50 is held stationary to counteract any tension applied to the anchor rail 22 and its anchor 26. Additionally, the strong anchor formed by the coupling of the shaft anchor 60 within the repair catheter shaft 24 is important to prevent decoupling. Tension exerted on the proximal end of the shaft extension member 62 helps to increase the anchoring force by expanding the midsection 72 of the shaft anchor 60, as was described above with respect to FIG. 4D.

FIGS. 7D and 7E show an alternative to the just-described embodiment, and specifically the system in FIG. 1A with a removal catheter 82 advanced into the subclavian vein and initial retraction of the catheter shaft 24 and the coapting element 30 thereon from within the tricuspid valve. In the alternative embodiment, the percutaneous heart valve regurgitation reduction system has no anchor rail, and thus the retrieval system need only grasp onto one tube, as opposed to concentric tubes. The steps shown in FIGS. 3-4 are followed to attach the shaft extension member 62 to the catheter shaft 24 via the expandable anchor 60. As mentioned, a coextensive outer diameter of the assembly of the shaft anchor 60 and extension 62 is sized to pass within the lumen of the catheter shaft 24. FIG. 4B shows the shaft anchor 60 radially outwardly extended within the catheter shaft 24 and coupled thereto, with the shaft extension member 62 extending proximally therefrom. The alternative system has no need for the anchor rail extension 50 as there is no anchor rail 22. Otherwise, the two systems are alike, with the shaft anchor 60 taking an of the forms as described herein.

Subsequently, the removal catheter 80 is advanced over the catheter shaft 24. The removal catheter 80 may be as described above and comprise the elongated sheath 82 having an inner luminal diameter sized large enough to pass over the assembly of the shaft anchor 60 and extension 62. An elongated device retrieval catheter 84 passes through the proximal hub 86 of the removal catheter 80 and has a length that enables it to extend through and beyond a distal end of the elongated sheath 82. A distal end of the retrieval catheter 84 again includes the expandable retrieval cage 85, while a proximal end has the hub 88 with hemostasis valves therein. The inner luminal diameter of the retrieval catheter 84 including the retrieval cage 85 is also sized large enough to pass over the assembly of the shaft anchor 60 and extension 62.

With reference to FIG. 7D, the removal catheter sheath 82 advances over the catheter shaft 24 and along a predetermined distance of the subclavian vein SV and halts approximately at the beginning of the superior vena cava SVC, as shown in FIG. 7E. FIG. 7D illustrates proximal retraction of the repair catheter shaft 24 toward the removal sheath 82 such that the coapting element 30 eventually comes into proximity with the distal end of the removal sheath. During this process, the strong anchor formed by the coupling of the shaft anchor 60 within the repair catheter shaft 24 is important to prevent decoupling. Tension exerted on the proximal end of the shaft extension member 62 helps to increase the anchoring force by expanding the midsection 72 of the shaft anchor 60, as was described above with respect to FIG. 4D.

The alternative embodiment of FIGS. 1A and 7D/7E represents any number of retrieval systems that may be used to couple to a singular tube within the body for retrieval thereof. That is, the shaft anchor 60 and extension 62 that pass within the lumen of the catheter shaft 24 may be utilized to couple to any tubular implant or instrument within the body that requires removal, or simply an extension therefor.

Figure 8A:
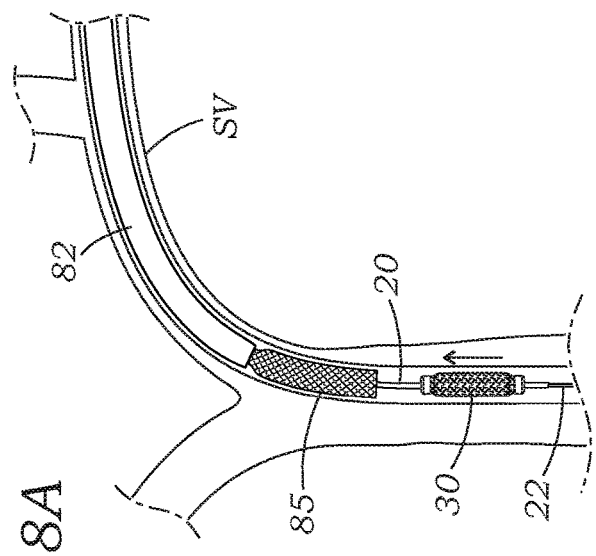
FIGS. 8A-8D are enlarged views of a distal end of the removal sheath showing several steps in utilizing a retrieval cage to draw the coapting element into the removal sheath.
Figure 8B:
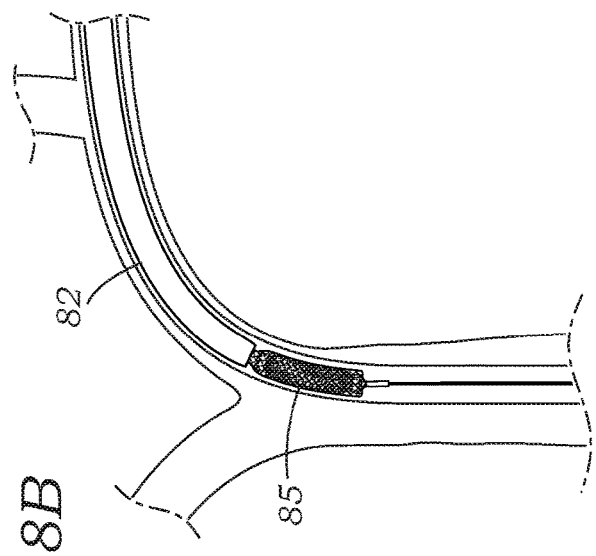
Figure 8C:
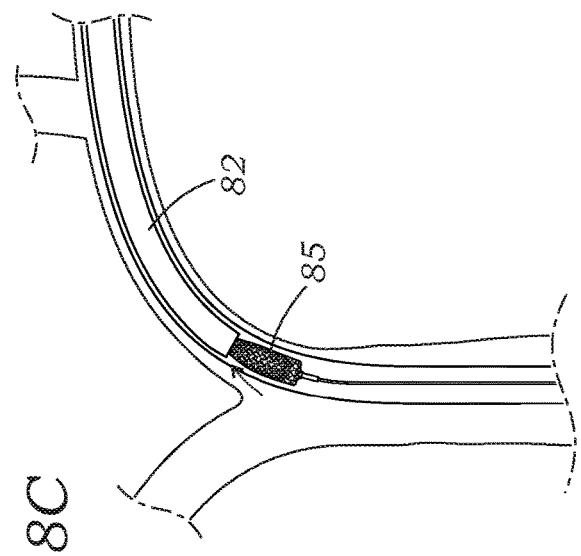
Figure 8D:
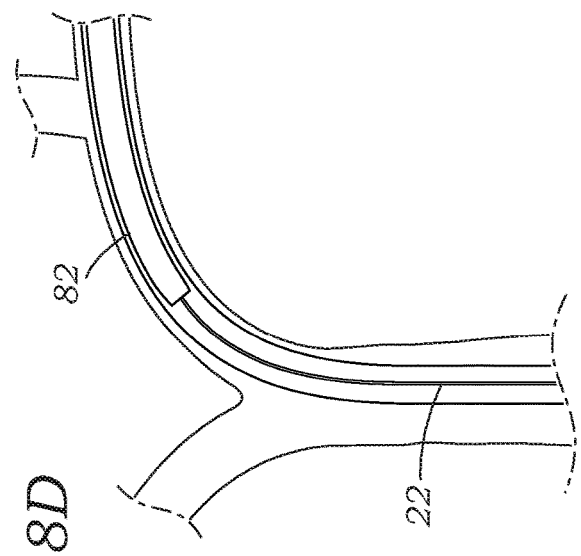

FIGS. 8A-8D are enlarged views of a distal end of the removal sheath 82 showing several steps in utilizing the retrieval cage 85 to draw the coapting element 30 into the removal sheath 82. First of all, the retrieval catheter 84 is advanced such that the retrieval cage 85 projects distally from the distal end of the removal sheath 82. The retrieval cage 85 is elastic in nature and expands to a larger diameter than the coapting element 30, and has an open distal end. By then proximally retracting the repair catheter shaft 24 via the shaft extension member 62, the coapting element 30 may be pulled within the retrieval cage 85, as in FIG. 8B. Subsequent retraction of the retrieval cage 85, as indicated in FIG. 8C, causes it to be pulled into the narrower removal sheath 82, simultaneously constricting the coapting element 30 and pulling it along into the removal sheath. Finally, the repair catheter shaft 24 and its extension 62 are fully removed from within the removal sheath 82, as in FIG. 8D.

Figure 9A:
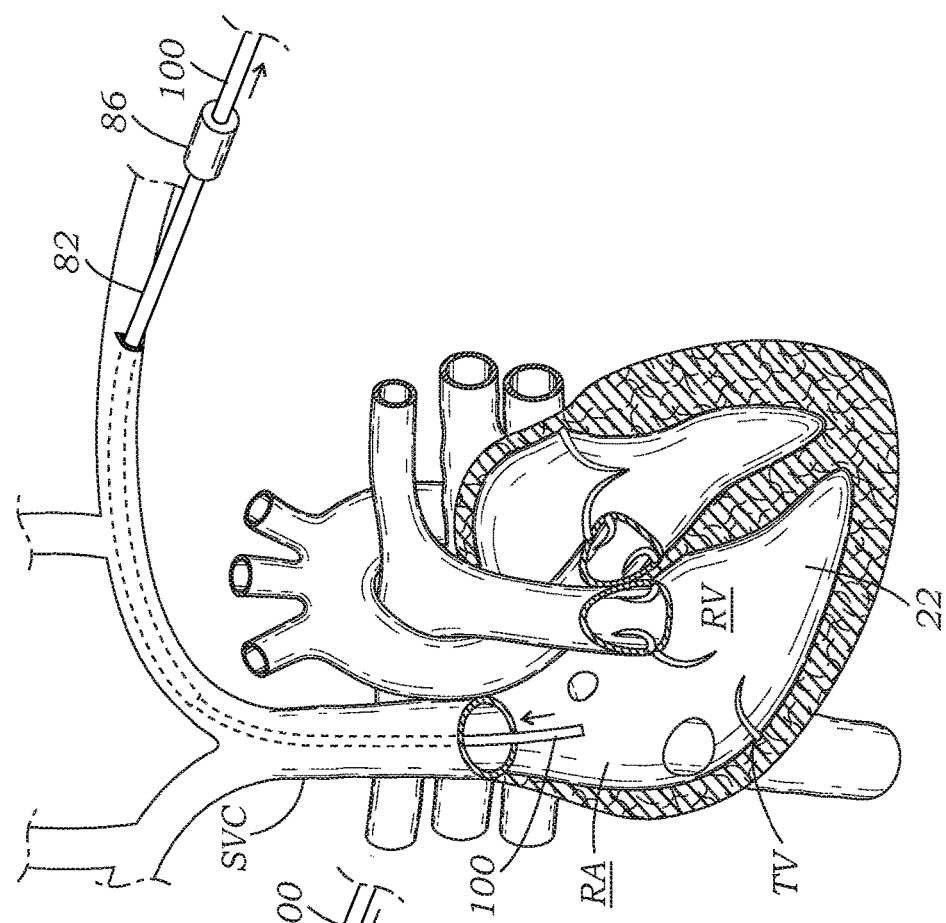
FIGS. 9A and 9B show advancement of a rail removal device through the removal sheath and subsequent removal of the anchor rail from its embedded position within the right ventricle.
Figure 9B:
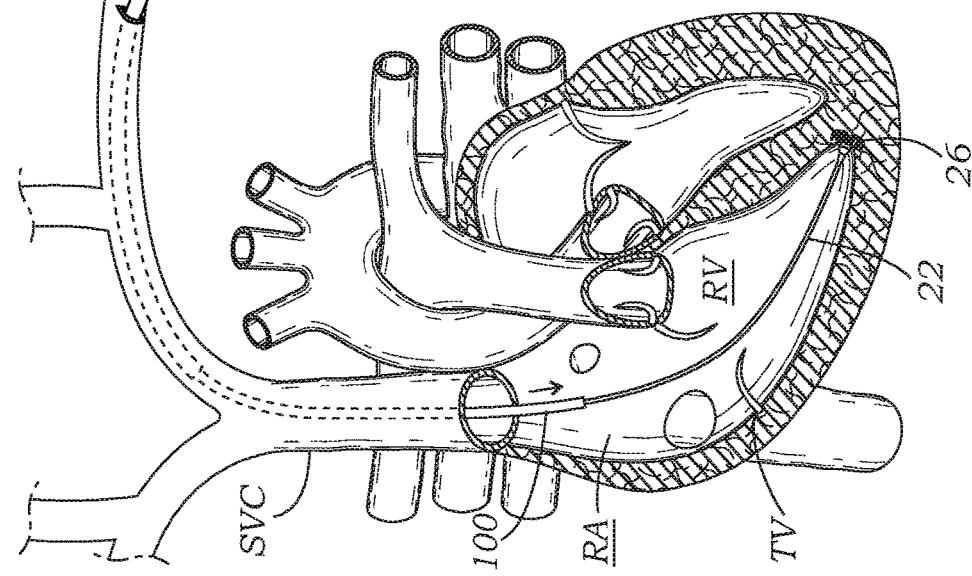

FIGS. 9A and 9B show advancement of a rail removal device 100 through the removal sheath 82 and subsequent removal of the anchor rail 22 from its embedded position within the right ventricle. FIG. 9A shows advancement of the rail removal device 100 through the removal sheath into proximity with the rail anchor 26. The rail removal device 100 may be the delivery system that originally implanted the rail 22 and its anchor 26. The rail removal device 100 is advanced until it surrounds an anchor hub, just proximal to the anchor 26, at which point the rail 22 may be pulled proximally via the rail extension member 50 to retract the prongs of the anchor 26 into the removal device. The entire system can then be retracted through the sheath from the body, as seen in FIG. 9B.

At this stage, another valve repair system may be inserted through the removal sheath 82, or through a different access tube, to position a different coapting element within the tricuspid annulus.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method for retrieving an elongated percutaneously-implanted implant or instrument having concentrically-disposed inner and outer tubes that each define lumens, comprising:

accessing proximal ends of both of the inner and outer tubes, the inner tube projecting proximally from within the outer tube;

attaching a first extension member to the inner tube with a first connector, the first extension member having a first length; and attaching a tubular second extension member to the outer tube with a second connector, the second extension member having a second length shorter than the first length, the second extension member having an inner lumen sufficiently large to slide over the first extension member, first connector, and inner tube, and having an outer diameter small enough to fit within the outer tube lumen, wherein at least one of the first and second connectors comprises an expandable auxetic section that radially expands outward into contact with the respective inner or outer tube lumen when subjected to a tensile force.

2. The method of claim 1, wherein the percutaneously-implanted device comprises a heart valve regurgitation reduction system having a coapting element positioned within the tricuspid valve, the coapting element being mounted at a distal end of the outer tube and the outer tube being concentrically disposed over the inner tube.

3. The method of claim 2, wherein the coapting element is configured to expand and contract, and the method further includes advancing a removal sheath over both the first extension member and inner tube as well as over the second extension member and outer tube, and withdrawing the second extension member to pull the outer tube and coapting element within the removal sheath.

4. The method of claim 3, further including advancing a retrieval catheter having a retrieval cage at a distal end within the removal sheath, expelling the retrieval cage out of a distal end of the removal sheath, the retrieval cage being self-expanding, and retracting the second extension member and outer tube to pull the coapting element into the expended retrieval cage, then retracting the retrieval cage into the removal sheath to compress both the retrieval cage and coapting element therein.

5. The method of claim 3, wherein the inner tube defines an anchor rail having a distal anchor embedded in tissue of the right ventricle, and further including holding the first extension member and connected anchor rail stationary while withdrawing the second extension member to counteract any tension applied to the distal anchor.

6. The method of claim 1, further including severing the inner and outer tubes such that the inner tube projects proximally from within the outer tube.

7. The method of claim 1, wherein the expandable auxetic section includes distal barbs that are outwardly biased and point in a proximal direction so as to contact and anchor inside of the respective inner or outer tube lumen so as to provide an anchor against proximal movement of the respective inner or outer tube and create tension in the expandable auxetic section when the respective inner or outer tube is displaced proximally.

8. The method of claim 7, wherein the second connector is a tubular element with the expandable auxetic section laser cut into a midsection.

9. The method of claim 8, wherein the tubular element further includes a pair of diametrically-opposed eyeholes located proximal to the expandable auxetic section.

10. The method of claim 1, wherein the expandable auxetic section is formed on the second connector between the second extension member and the outer tube, and the first connector includes a crimp able hypo tube.

11. A method for retrieving a coapting element of an elongated percutaneously-implanted system having a tubular inner rail and a tubular outer shaft, the coapting element being disposed at a distal end of the outer shaft and within an atrioventricular heart valve, comprising:

accessing proximal ends of both of the inner rail and outer shaft, the inner rail projecting proximally from within the outer shaft;

attaching a first extension member to the inner rail with a first connector, the first extension member having a first length; and attaching a tubular second extension member to the outer shaft with a second connector having an outer diameter small enough to fit within a lumen of the outer shaft, the second extension member having a second length shorter than the first length, the second extension member having an inner lumen sufficiently large to slide over the first extension member, first connector, and inner rail, and having an outer diameter small enough to fit within the outer shaft lumen, wherein at least one of the first and second connectors comprises an expandable auxetic section that radially expands outward into contact with a respective inner or outer shaft lumen when subjected to a tensile force.

12. The method of claim 11, wherein the coapting element is positioned within the tricuspid valve, wherein the inner rail defines an anchor rail having a distal anchor embedded in tissue of the right ventricle.

13. The method of claim 11, wherein the coapting element is configured to expand and contract, and the method further includes advancing a removal sheath over both the first extension member and inner rail as well as over the second extension member and outer shaft, and withdrawing the second extension member to pull the outer shaft and coapting element within the removal sheath.

14. The method of claim 13, further including advancing a retrieval catheter having a retrieval cage at a distal end within the removal sheath, expelling the retrieval cage out of a distal end of the removal sheath, the retrieval cage being self-expanding, and retracting the second extension member and outer shaft to pull the coapting element into the expended retrieval cage, then retracting the retrieval cage into the removal sheath to compress both the retrieval cage and coapting element therein.

15. The method of claim 13, wherein the inner rail defines an anchor rail having a distal anchor embedded in heart tissue, and further including holding the first extension member and connected anchor rail stationary while withdrawing the second extension member to counteract any tension applied to the distal anchor.

16. The method of claim 11, further including severing the inner rail and outer shaft such that the inner rail projects proximally from within the outer shaft.

17. The method of claim 11, wherein the expandable auxetic section includes distal barbs that are outwardly biased and point in a proximal direction so as to contact and anchor inside of the respective lumen of the inner rail or outer shaft so as to provide an anchor against proximal movement of the respective inner or outer shaft and create tension in the expandable auxetic section when the respective inner rail or outer shaft is displaced proximally.

18. The method of claim 17, wherein the second connector is a tubular element with the expandable auxetic section laser cut into a midsection.

19. The method of claim 18, wherein the tubular element further includes a pair of diametrically-opposed eyeholes located proximal to the expandable auxetic section.

20. The method of claim 11, wherein the expandable auxetic section is formed on the second connector between the second extension member and the outer shaft, and the first connector includes a crimp able hypo tube.

* * * * *